(12) United States Patent
Kim et al.

(10) Patent No.: US 10,200,057 B2
(45) Date of Patent: Feb. 5, 2019

(54) METHOD FOR STABILIZING GAIN OF APD IN MEDICAL LASER RECEIVER

(71) Applicant: DANKOOK UNIVERSITY CHEONAN CAMPUS INDUSTRY ACADEMIC COOPERATION, Cheonan-si (KR)

(72) Inventors: Sehwan Kim, Yongin-si (KR); Phil-sang Chung, Cheonan-si (KR); Albert E. Cerussi, Cheonan-si (KR)

(73) Assignee: DANKOOK UNIVERSITY CHEONAN CAMPUS INDUSTRY ACADEMIC COOPERATION, Cheonan-Si (KR)

(*) Notice: Subject to any disclaimer, the term of this patent is extended or adjusted under 35 U.S.C. 154(b) by 515 days.

(21) Appl. No.: 14/901,599

(22) PCT Filed: Jun. 20, 2014

(86) PCT No.: PCT/KR2014/005456
§ 371 (c)(1),
(2) Date: Jun. 17, 2016

(87) PCT Pub. No.: WO2014/208931
PCT Pub. Date: Dec. 31, 2014

(65) Prior Publication Data
US 2016/0373126 A1    Dec. 22, 2016

(30) Foreign Application Priority Data

Jun. 27, 2013    (KR) ........................ 10-2013-0074949

(51) Int. Cl.
*H03M 1/12*    (2006.01)
*H03G 3/30*    (2006.01)
(Continued)

(52) U.S. Cl.
CPC ............... *H03M 1/12* (2013.01); *A61B 5/00* (2013.01); *H01L 31/02027* (2013.01);
(Continued)

(58) Field of Classification Search
CPC ............ G02B 6/12007; G02B 6/122; G02B 6/12004; G02B 6/124; G02B 2006/12138;
(Continued)

(56) References Cited

U.S. PATENT DOCUMENTS

| 4,438,348 A | 3/1984 | Casper et al. |
| 7,009,184 B2 * | 3/2006 | Temple-Boyer ......... G01D 3/06 250/214 A |

FOREIGN PATENT DOCUMENTS

| JP | 2005-354485 A | 12/2005 |
| JP | 2006-156808 A | 6/2006 |
| KR | 2004-0062334 A | 7/2004 |

OTHER PUBLICATIONS

International Search Report, dated Sep. 23, 2014, for PCT/KR2014/005456, with English translation, 4 pages.

* cited by examiner

*Primary Examiner* — Tony Ko
(74) *Attorney, Agent, or Firm* — Seed IP Law Group LLP

(57) ABSTRACT

The present invention provides a method for stabilizing the gain of an avalanche photodiode in a medical laser diode receiver. This method is characterized by comprising: (a) a step in which a high-voltage generation unit generates a high-voltage bias and applies same to an avalanche photodiode; (b) a step in which a temperature sensor senses the temperature of the avalanche photodiode; (c) a step in which a control unit controls a variable resistance value, which varies the voltage of the high-voltage bias, according to the value of the sensed temperature; (d) a step in which to detect if an output voltage signal is equivalent to the intensity of
(Continued)

light received by the avalanche photodiode; and (e) a step in which a storage unit matches the sensed temperature value with the controlled variable resistance value and stores same. The present invention allows a reduction in production costs and also a significant reduction in the size of a measuring device itself. In addition, the present invention can prevent measurement errors by stabilizing the voltage gain of the avalanche photodiode and can promote precise diagnosis by accurately measuring scattered light even in a highly curved part of a human body to be measured by passing the light of a laser diode therethrough.

5 Claims, 6 Drawing Sheets

(51) Int. Cl.
    *H01L 31/02*          (2006.01)
    *H01L 31/107*        (2006.01)
    *A61B 5/00*          (2006.01)
    *A61B 18/20*         (2006.01)
    *A61B 18/00*         (2006.01)

(52) U.S. Cl.
    CPC ......... *H01L 31/107* (2013.01); *H03G 3/3084* (2013.01); *A61B 18/20* (2013.01); *A61B 2018/00642* (2013.01); *A61B 2018/00714* (2013.01); *A61B 2018/00767* (2013.01); *A61B 2018/00791* (2013.01); *A61B 2018/00892* (2013.01)

(58) Field of Classification Search
    CPC .. G02B 2006/12104; G01J 1/44; G01J 1/0488
    See application file for complete search history.

METHOD FOR STABILIZING GAIN OF APD IN MEDICAL LASER RECEIVER

TECHNICAL FIELD

The present invention relates to a method for stabilizing a gain of an APD, and more particularly, to a method for stabilizing a gain of an APD of a medical laser receiver that can stabilize response characteristics of an avalanche photodiode of which a voltage gain is changed according to backward voltage and temperature, in a medical device that uses a laser diode for an optical medical diagnosis.

BACKGROUND ART

In general, an avalanche photodiode (APD) is a photodiode having rapid speed and high response characteristics, and is an element that internally generates an electrical signal by adjusting amplitude ratio according to a change in backward voltage.

In particular, the avalanche photodiode used in an optical medical device is packaged in a TO can form, and is used to measure characteristics of light when the light output from a laser diode passes through a portion of a tissue of the human body and is introduced into the avalanche photodiode.

Most of the light is lost due to absorption and scattering of light while passing through the human body so that only a very small amount of light is introduced into the avalanche photodiode, and an avalanche photodiode that mostly uses a reverse bias voltage of not less than 100 V is used to achieve an avalanche photodiode having a high light receiving gain.

However, because the avalanche photodiode has characteristics in which a voltage gain is changed according to a backward voltage value, a high amplitude ratio is achieved by increasing a backward voltage value.

However, because the avalanche photodiode has an allowable maximum voltage value, voltage amplitude radio increases geometrically if voltage value exceeds the limit value, so that the avalanche photodiode is burned out.

Further, a voltage gain of the avalanche photodiode is changed according to temperature.

The reason why amplitude ratio is changed according to temperature is that the temperature increases as the lattice structure of the avalanche photodiode vibrates, and then the number of carriers increases so that energy level is moved by an ionization phenomenon.

Due to this phenomenon, amplitude ratio changes according to temperature even at the same backward voltage, and response characteristics of the avalanche photodiode are changed as the amplitude ratio changes so that measurement time changes even when the same amount of light is introduced into the avalanche photodiode.

When the avalanche photodiode having the characteristics makes direct contact with the human body to measure scattering light, light receiving gain also rapidly changes as operation temperature rapidly changes due to body temperature as a result of the contact.

Further, even when the avalanche photodiode does not make direct contact, the temperature of the avalanche photodiode changes due to a peripheral circuit, a voltage supply unit, or the like.

This mainly causes a measurement error of a medical device that uses a laser diode.

According to the related art, in order to overcome the problems, a technology of constantly maintaining the temperature of an avalanche photodiode by employing a thermoelectric cooler (TEC) outside an avalanche photodiode TO-can.

FIG. 1 is a perspective view of an external appearance of a laser diode measuring apparatus using a thermoelectric cooler according to the related art, and includes an avalanche photodiode 10, a thermoelectric cooler 20, a heat sink, and a cooling fan 30.

The laser diode measuring apparatus using the thermoelectric cooler 20 has heat emitting and cooling functions through a forward current and a backward current, and constantly maintains amplitude ratio by preventing a temperature change of the avalanche photodiode 10 by controlling temperature through an external control unit.

In order to use the thermoelectric cooler 20, a thermistor for detecting the temperature of an avalanche photodiode 10 and a current supply circuit for driving an thermoelectric cooler 20 should be inevitable included.

In addition to an increase of power consumption and costs, as illustrated in FIG. 1, there is a limit in that the size of the measurement apparatus is very large.

Accordingly, in an optical diagnosis system using an avalanche photodiode 10, in particular, in a structure in which scattering light should be measured by bringing the avalanche photodiode into direct contact with a surface of skin, because the size of the measurement apparatus should be large, there are many problems in measuring a severely curved portion, for example, in measuring a thyroid gland of a neck, a sentinel lymph node, or the like.

DISCLOSURE

Technical Problem

An object of the present invention is to provide a method for stabilizing a gain of an APD of a medical laser receiver in which a voltage level of the high-voltage bias of the avalanche photodiode that changes according to temperature is controlled by receiving a laser diode ray and comparing the output voltage data for the intensity of output light with the magnitude of the reference voltage at a room temperature to control variable resistance by the photodiode.

Technical Solution

In order to solve the above-mentioned problems, there is provided a method for stabilizing a gain of an APD of a medical laser receiver, the method including the steps of: (a) generating a high-voltage bias and applying the generated high-voltage bias to an avalanche photodiode by a high-voltage generating unit; (b) detecting the temperature of the avalanche photodiode by a temperature sensor; (c) controlling a variable resistance value that changes the voltage of the high-voltage bias according to the detected temperature value by a control unit; (d) detecting whether the same voltage signal is output for intensities of light received by the avalanche photodiode; and (e) matching the detected temperature value and the controlled variable resistance value and storing the matching result by a storage unit.

The method for achieving the object further includes the steps of: after step (e), (f) receiving the voltage signal and converting the received voltage signal into digital temperature data by the AD converter; (g) increasing or decreasing the controlled temperature by a first temperature; and (h) comparing output voltage data of the avalanche photodiode with the magnitude of the reference voltage to automatically control the variable resistance value.

In the method for achieving the object, step (h) includes: when the output voltage of the avalanche photodiode is lower than the reference voltage, decreasing the variable resistance value.

In the method for achieving the object, step (h) further includes: when the output voltage of the avalanche photodiode is higher than the reference voltage, increasing the variable resistance value.

In the method for achieving the object, step (a), the avalanche photodiode receives laser diode light at room temperature and outputs a voltage signal for the intensity of the light, the AD converter receives a voltage signal at room temperature and converts the applied voltage signal into digital temperature data, the control unit receives the digital temperature data and stores the received digital temperature data in the storage unit as a reference voltage, and the storage unit reads a variable resistance value at room temperature and stores the read variable resistance value in a storage area corresponding to room temperature as a reference resistance.

In the method for achieving the object, the first temperature is set to 1° C. to 3° C.

Advantageous Effects

According to the present invention, because a thermistor and a current supply circuit used for a thermoelectric cooler are not necessary, manufacturing costs can be reduced and the size of the measurement device can be remarkably reduced.

Furthermore, even though operation temperature rapidly changes due to body temperature or an influence of a surrounding environment, a measurement error can be prevented by controlling a voltage level of a high-voltage bias of an avalanche photodiode to stabilize a voltage gain of the APD, and a precise diagnosis can be achieved by accurately measuring scattering light even on a severely curved portion of the human body as laser diode light passes through the portion of the human body.

DESCRIPTION OF THE INVENTION

BEST MODE

Hereinafter, a method for stabilizing a gain of an APD of a medical laser receiver according to the present invention will be described with reference to the accompanying drawings.

Figure 1:
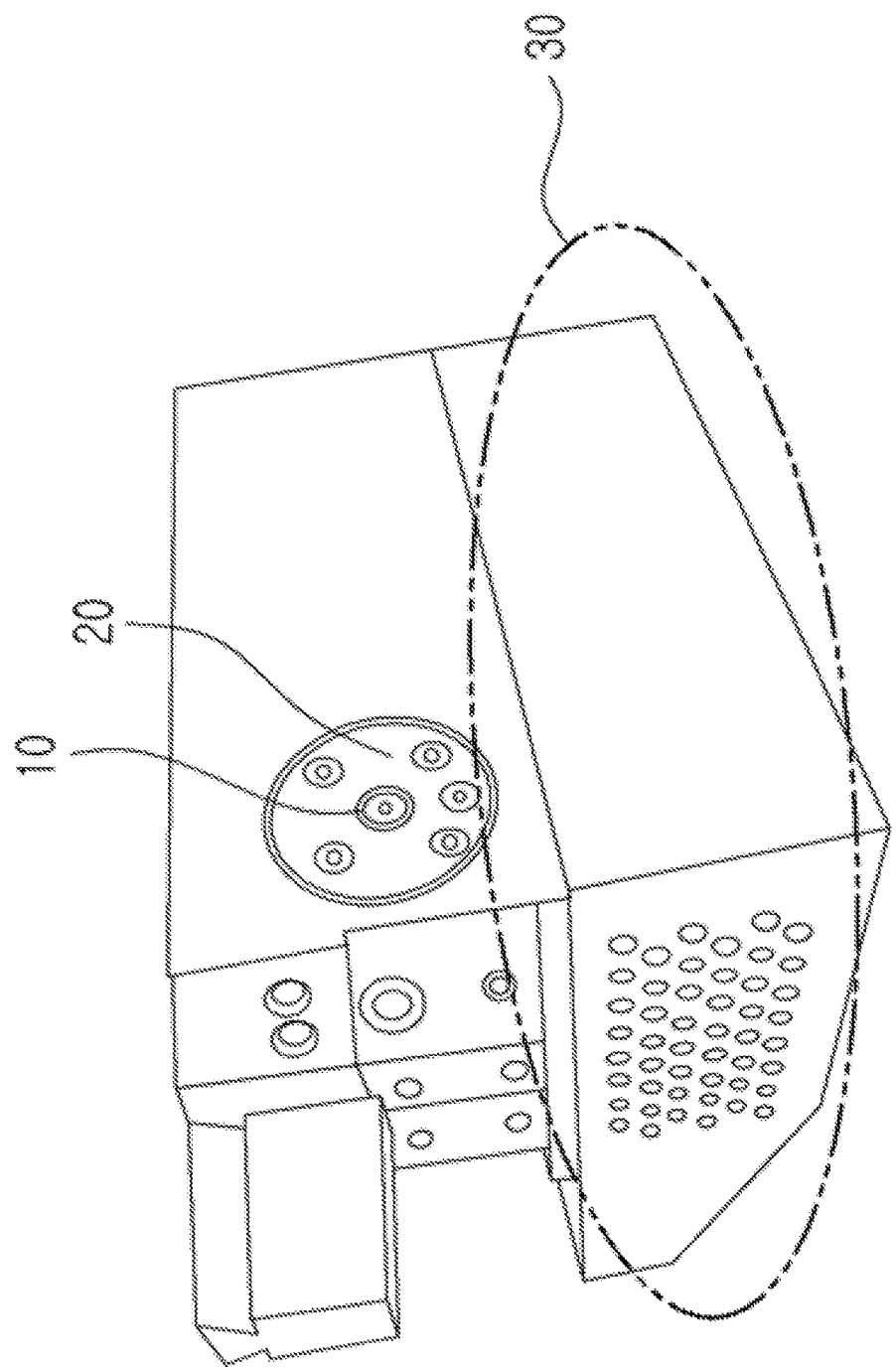
FIG. 1 is a perspective view illustrating an external appearance of a laser diode measuring apparatus using a thermoelectric cooler according to the related art.
Figure 2:
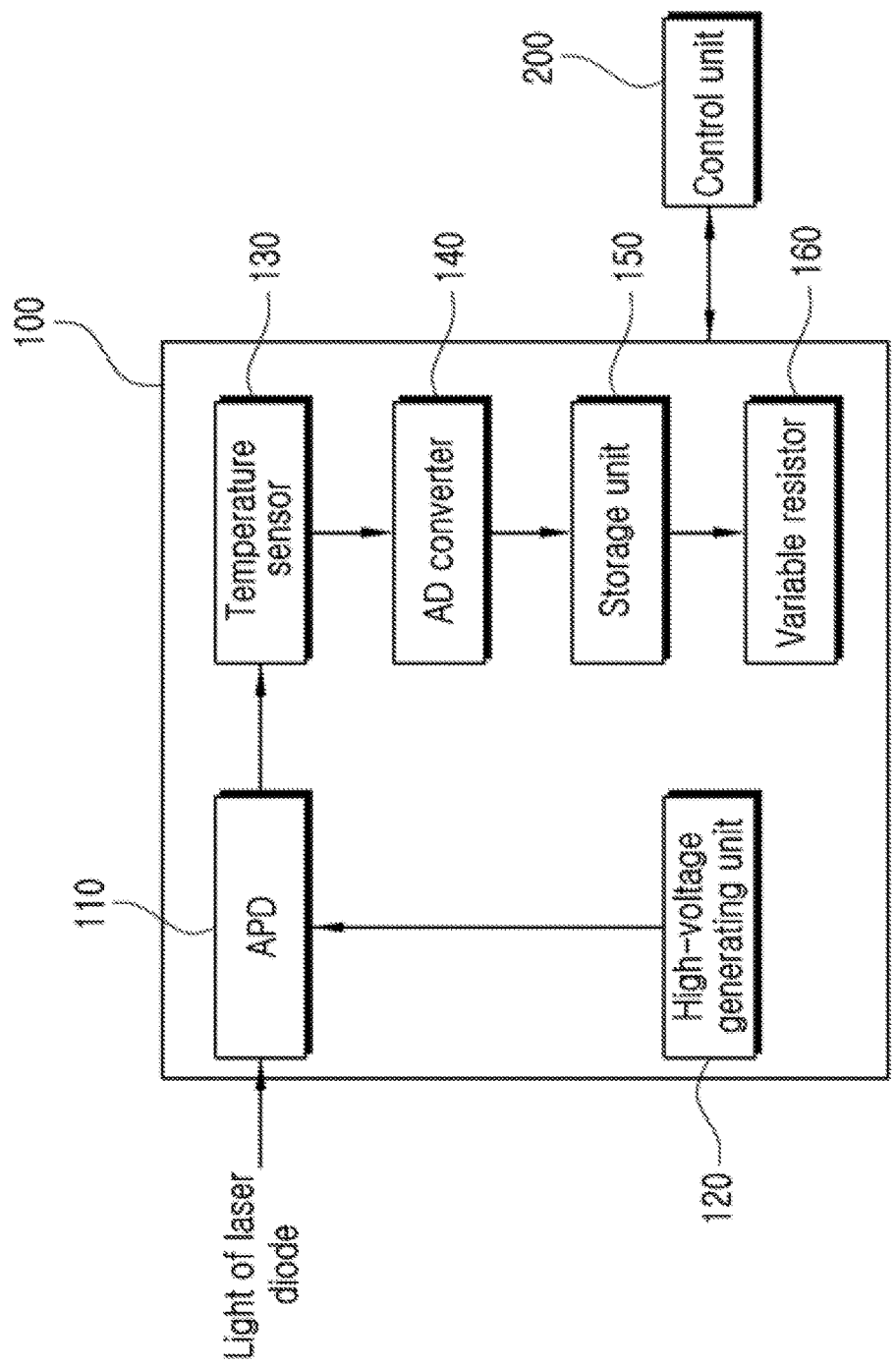
FIG. 2 is a block diagram of an apparatus for stabilizing a gain of an APD of a medical laser receiver according to the present invention.

FIG. 2 is a block diagram of an apparatus for stabilizing a gain of an APD of a medical laser receiver according to the present invention, and the apparatus includes an avalanche photodiode receiver 100 and a control unit 200 and the avalanche photodiode receiver 100 includes an avalanche photodiode 110, a high-voltage generating unit 120, a temperature sensor 130, an AD converter 140, a storage unit 150, and a variable resistor 160.

Referring to FIG. 2, the functions of the components of the apparatus for stabilizing a gain of an APD of a medical laser receiver according to the present invention will be described as follows.

The avalanche photodiode 110 receives light of a laser diode after the light output from the laser diode passes through a portion of a human tissue and outputs a voltage signal for the intensity of the light, and a light receiving gain varies according to temperature and a reverse bias voltage.

The high-voltage generating unit 120 generates a high-voltage bias and supplies the generated high-voltage bias to the photodiode 110. A bias voltage level that is output is controlled by inputting a voltage in a predetermined range that may be controlled through a control input pin.

The temperature sensor 130 detects and outputs the temperature of the avalanche photodiode 110.

The AD converter 140 receives a temperature value detected by the temperature sensor 130 and converts the received temperature value into digital temperature data.

The control unit 200 controls a variable resistance at the detected temperature, and controls the voltage output from the avalanche photodiode 110 such that the voltage output from the avalanche photodiode 110 is the same as a reference voltage, and stores the variable resistance value at the detected temperature in the storage unit 150.

The variable resistor 160 is a digital variable resistor that presets a desired resistance value such that the resistance value is changed to the desired resistance value at a specific temperature, and automatically increases or decreases to a resistance value at the corresponding temperature.

Through this, the voltage level of the high-voltage bias generated by the high-voltage generating unit 120 is automatically controlled within a predetermined voltage range necessary for a voltage control input.

A detailed operation of controlling a variable resistance according to a temperature change and storing the controlled variable resistance by the control unit 200 will be described in the following.

Figure 3:
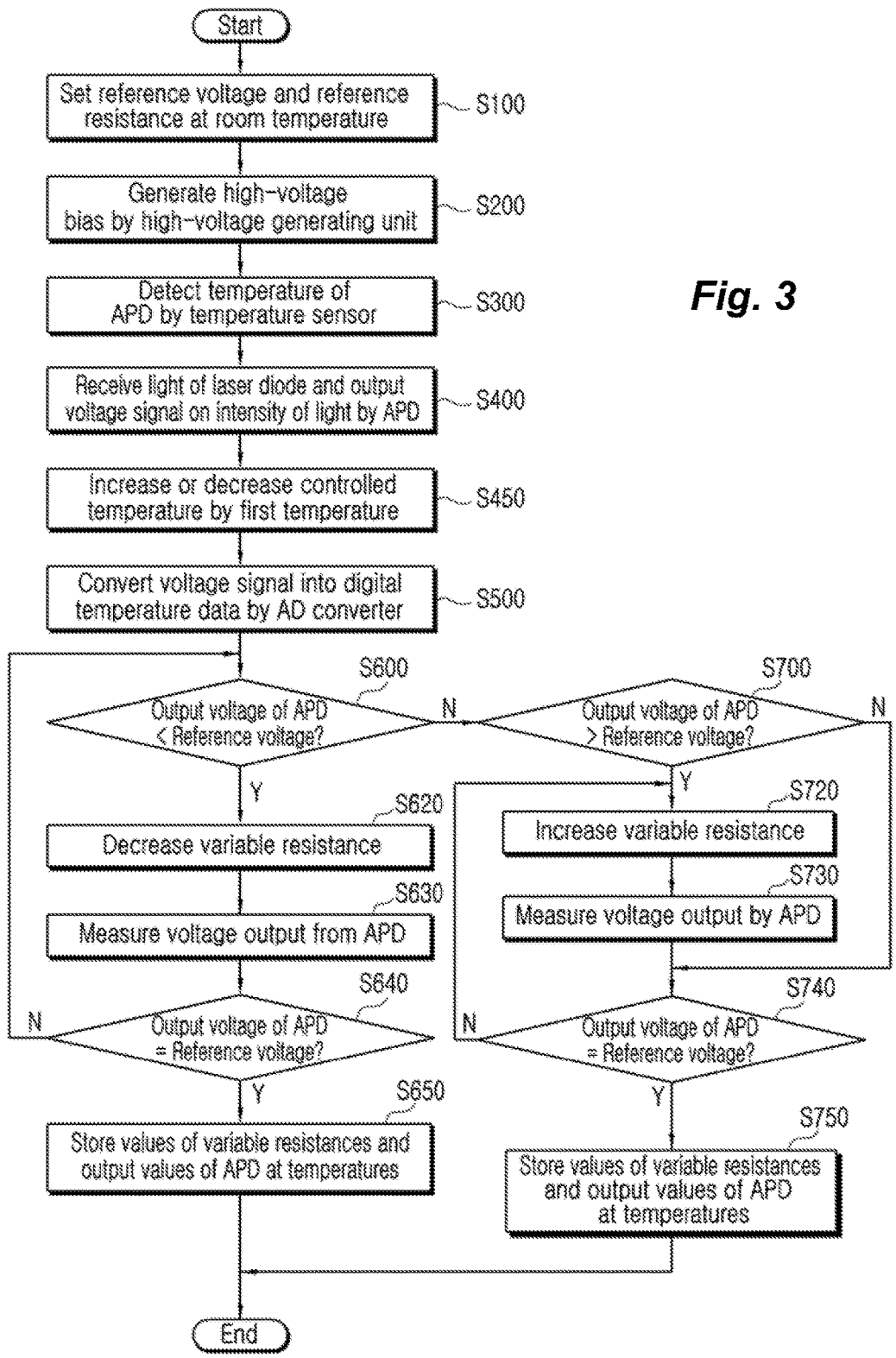
FIG. 3 is a flowchart illustrating an operation of a method for stabilizing a gain of an APD of a medical laser diode receiver according to the present invention.

FIG. 3 is a flowchart illustrating an operation of a method for stabilizing a gain of an APD of a medical laser diode receiver according to the present invention.

Figure 4:
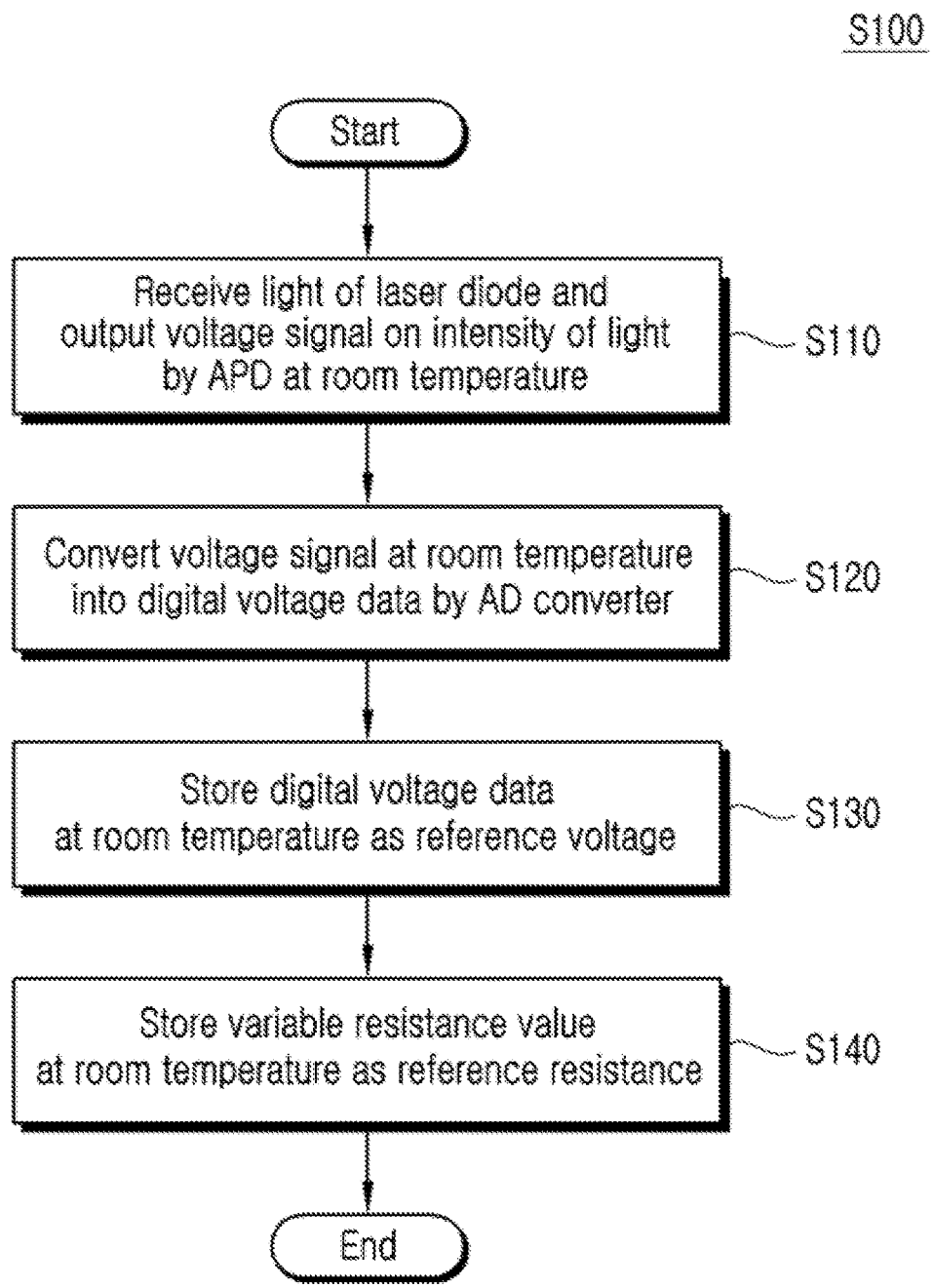
FIG. 4 is a flowchart illustrating a detailed operation of step S100 in FIG. 3.

FIG. 4 is a flowchart illustrating a detailed operation of step S100 in FIG. 3.

Figure 5:
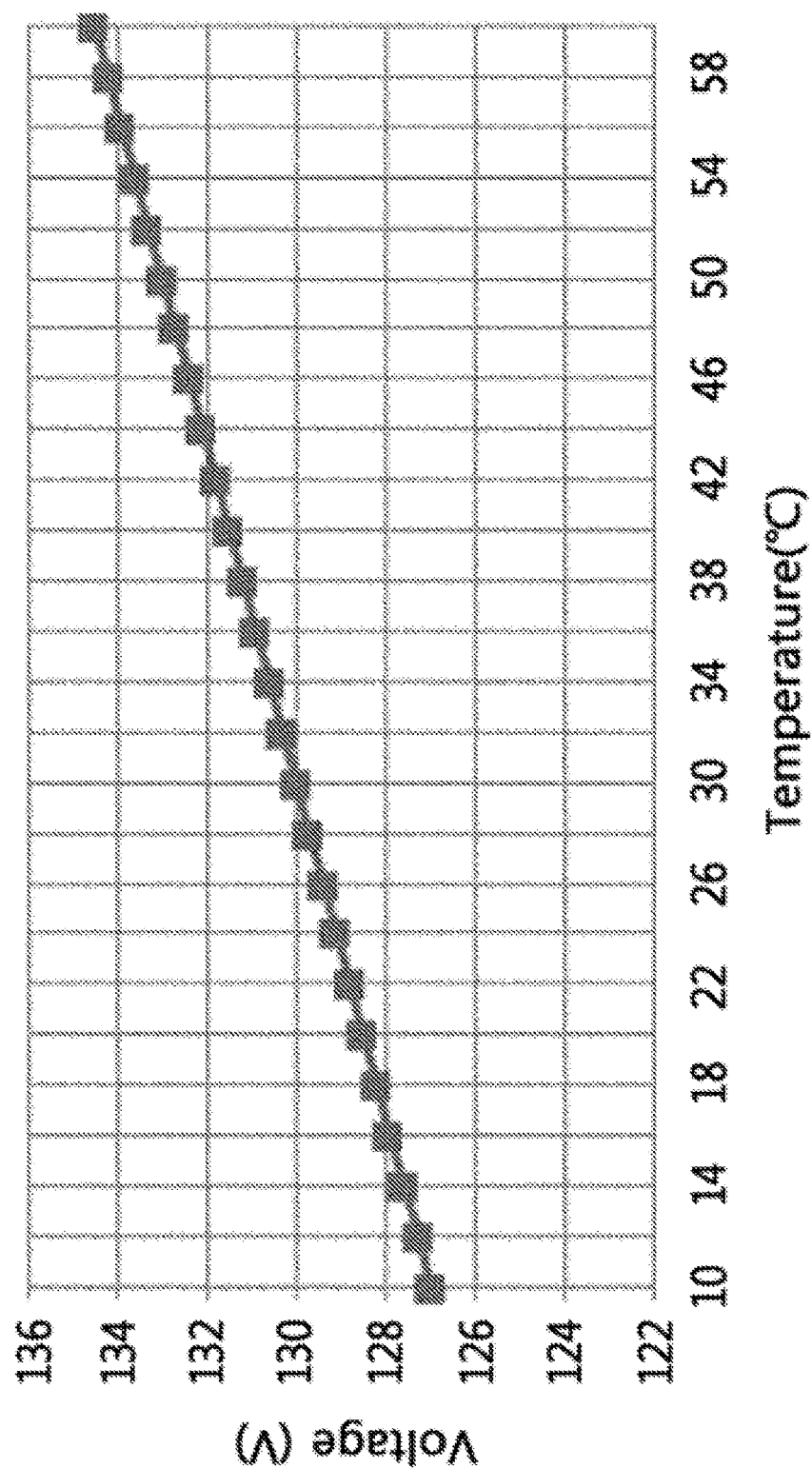
FIG. 5 is a graph depicting a change in APD bias voltage to a temperature change according to the present invention.

FIG. 5 is a graph depicting a change in APD bias voltage to a temperature change according to the present invention.

Figure 6:
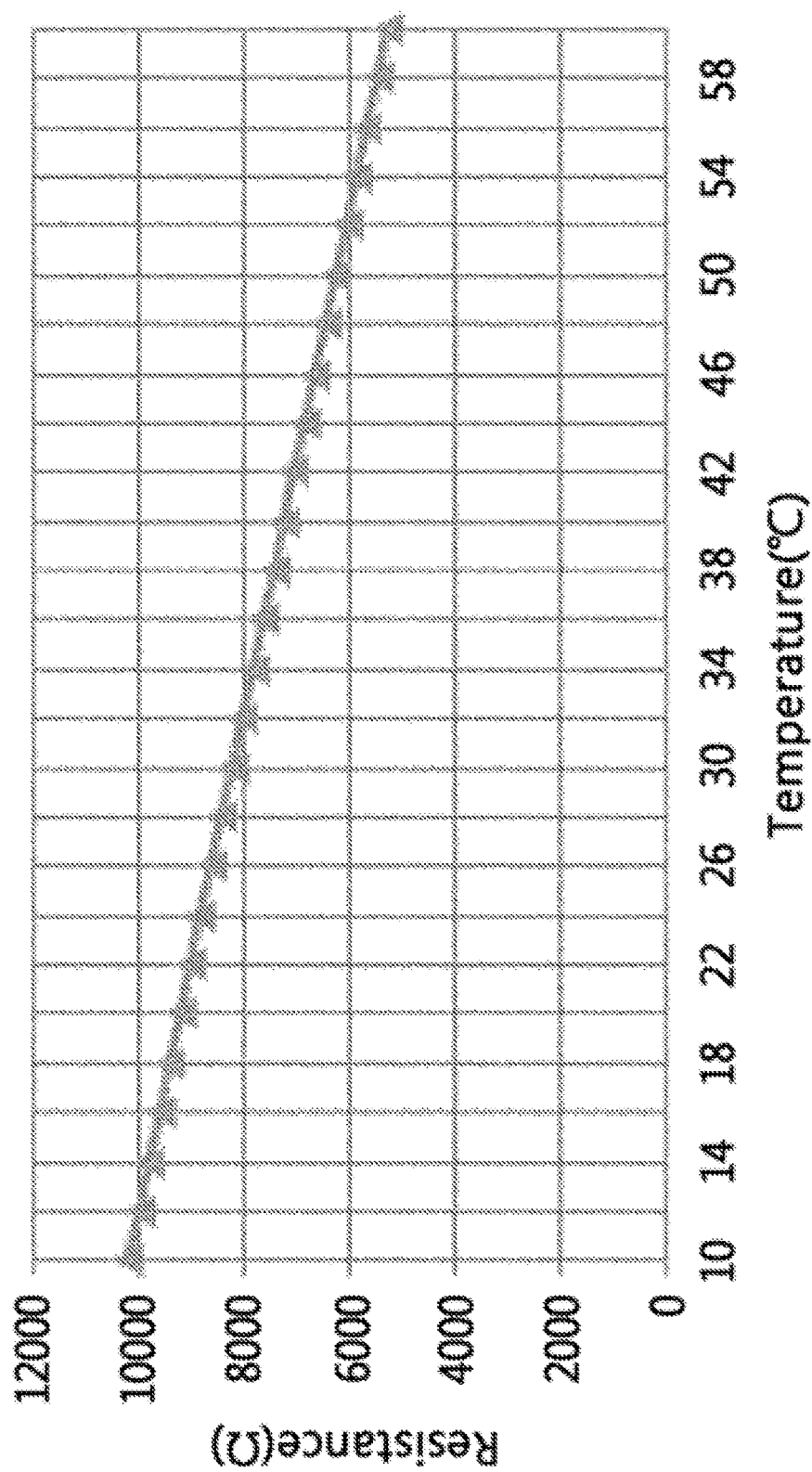
FIG. 6 is a graph depicting a change in variable resistance value to a temperature change according to the present invention.

FIG. 6 is a graph depicting a change in value of the variable resistor 160 to a temperature change according to the present invention.

Referring to FIGS. 2 to 6, an operation of an embodiment of the apparatus for stabilizing a gain of an APD of a medical laser diode receiver according to the present invention will be described as follows.

First, the control unit 200 sets a reference temperature which a laser diode receiver, on which the avalanche photodiode 110 is mounted, meets to a room temperature of 25° C.

The avalanche photodiode 110 receives laser diode light generated by a laser diode at room temperature, adjusts amplification ratio according to a change in backward voltage by using high electric power generated by a high-power generating unit, and outputs a voltage signal for the intensity of light at the detected ambient temperature.

The AD converter 140 converts the corresponding room temperature into digital temperature data, and the control unit 200 adjusts a backward voltage of the avalanche photodiode by controlling a variable resistance to control an output voltage signal of the avalanche photodiode to a reference voltage value corresponding to the corresponding room temperature.

Then, the control unit 200 reads a variable resistance value in the variable resistance unit for controlling temperature, and stores the resistance value in a storage area of the storage unit 150 corresponding to the room temperature (S100).

The high-voltage generating unit 120 generates and supplies a high-voltage bias of not less than 100 V (S200).

The temperature sensor 130 detects a current temperature the APD gain stabilizing apparatus according to the present invention, on which the avalanche photodiode 110 is mounted, meets (S300).

The avalanche photodiode 110 receives laser diode light generated by the laser diode at room temperature, adjusts amplification ratio according to a change in backward voltage by using high electric power generated by the high-power generating unit, and outputs a voltage signal for the intensity of light at the detected current temperature (S400).

The controlled temperature increases or decreases by a first temperature (S450), and the AD converter 140 converts the detected current temperature value into digital temperature data (S500).

When the output voltage data of the avalanche photodiode for the intensity of light at the changed temperature is lower than the reference voltage, a voltage output by the avalanche photodiode 110 is measured (S630) while the variable resistance is decreased (S620).

Here, the first temperature may be set to 1° to 3° C., and preferably to 2° C. The operation continues until the output voltage measured by the avalanche photodiode 110 increases to the magnitude of the reference voltage stored in advance (S640), and then the value of the variable resistance is stored in the corresponding storage area of the storage unit 150 (S650).

If the voltage data for the intensity of light at the current temperature is higher than a reference voltage (S700), the variable resistance is increased (S720), and the voltage output by the avalanche photodiode 110 is measured (S730).

The operation continues until the output voltage measured by the avalanche photodiode 110 decreases to the magnitude of the reference voltage (S740), and then the value of the variable resistance is stored in the storage unit 150 (S750).

Variable resistance values are found at the temperatures through the method, and are stored in the storage unit 150.

Because a variable resistance is automatically controlled according to a temperature change after the variable resistance values are matched with the temperatures and are stored through the method, the control unit 200 does not perform a variable resistance control operation.

That is, as illustrated in FIG. 5, because the variation of the voltage level of a high-voltage bias is induced by increasing or decreasing the value of the variable resistor 160 by using the voltage distribution law, a gain of the avalanche photodiode 110 can be stabilized by increasing or decreasing the bias voltage value of the avalanche photodiode 110 that increases according to temperature as illustrated in FIG. 6.

In this way, in the method for stabilizing a gain of an APD of a medical laser receiver according to the present invention, a voltage level of the high-voltage bias of the avalanche photodiode that changes according to temperature is controlled by receiving a laser diode ray and comparing the output voltage data for the intensity of output light with the magnitude of the stored reference voltage at a room temperature to control variable resistance by the photodiode.

Through this, because a thermistor and a current supply circuit used for a thermoelectric cooler are not necessary, manufacturing costs can be reduced and the size of the measurement device can be remarkably reduced.

Furthermore, even though operation temperature rapidly changes due to body temperature, a measurement error can be prevented by controlling a voltage level of a high-voltage bias of an avalanche photodiode to stabilize a voltage gain of the APD, and a precise diagnosis can be achieved by accurately measuring scattering light even on a severely curved portion of the human body as laser diode light passes through the portion of the human body.

Although the preferred embodiments of the present invention have been described, it will be understood by those skilled in the art that the present invention can be variously corrected and modified without departing from the spirit and scope of the present invention claimed in the claims.

The invention claimed is:

1. A method for stabilizing a gain of an APD of a medical laser receiver, the method comprising the steps of:
    (a) generating a high-voltage bias and applying the generated high-voltage bias to an avalanche photodiode by a high-voltage generating unit;
    (b) detecting the temperature of the avalanche photodiode by a temperature sensor;
    (c) controlling a variable resistance value that changes the voltage of the high-voltage bias according to the detected temperature value by a control unit;
    (d) detecting whether the same voltage signal is output for intensities of light received by the avalanche photodiode; and
    (e) matching the detected temperature value and the controlled variable resistance value and storing the matching result by a storage unit,
    wherein the avalanche photodiode, the high-voltage generating unit, an AD converter, and the storage unit, and a variable resistor are integrally embedded in a photodiode receiver chip, and
    wherein before step (a), the avalanche photodiode receives laser diode light at room temperature and outputs a voltage signal for the intensity of the light, the AD converter receives a voltage signal at room temperature and converts the applied voltage signal into digital temperature data, the control unit receives the digital temperature data and stores the received digital temperature data in the storage unit as a reference voltage, and the storage unit reads a variable resistance value at room temperature and stores the read variable resistance value in a storage area corresponding to room temperature as a reference resistance, and
    wherein after the detected temperature value and the controlled variable resistance value are stored, the variable resistance value is automatically controlled according to a temperature change without being controlled by the control unit.

2. The method according to claim 1, further comprising the steps of:
    after step (e),
    (f) receiving the voltage signal and converting the received voltage signal into digital temperature data by the AD converter;

(g) increasing or decreasing the controlled temperature by a first temperature; and
(h) comparing output voltage data of the avalanche photodiode with the magnitude of the reference voltage to automatically control the variable resistance value.

3. The method according to claim 2, wherein step (h) comprises: when the output voltage of the avalanche photodiode is lower than the reference voltage, decreasing the variable resistance value.

4. The method according to claim 3, wherein step (h) further comprises: when the output voltage of the avalanche photodiode is higher than the reference voltage, increasing the variable resistance value.

5. The method according to claim 3, wherein the first temperature is set to 1° C. to 3° C.

* * * * *